US012559708B2

(12) United States Patent
Maeda et al.

(10) Patent No.: US 12,559,708 B2
(45) Date of Patent: Feb. 24, 2026

(54) CELL COLLECTING DEVICE AND CELL COLLECTING METHOD

(71) Applicant: SHIMADZU CORPORATION, Kyoto (JP)

(72) Inventors: Yamato Maeda, Kyoto (JP); Akari Takeda, Kyoto (JP); Yoshitake Yamamoto, Kyoto (JP); Yoshitaka Noda, Kyoto (JP); Takashi Inoue, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 1074 days.

(21) Appl. No.: 17/628,528

(22) PCT Filed: Jul. 26, 2019

(86) PCT No.: PCT/JP2019/029514
§ 371 (c)(1),
(2) Date: Jan. 19, 2022

(87) PCT Pub. No.: WO2021/019624
PCT Pub. Date: Feb. 4, 2021

(65) Prior Publication Data
US 2022/0259542 A1 Aug. 18, 2022

(51) Int. Cl.
*C12M 1/00* (2006.01)
*C12M 1/26* (2006.01)

(52) U.S. Cl.
CPC ............ *C12M 33/04* (2013.01); *C12M 23/40* (2013.01); *C12M 29/00* (2013.01); *C12M 39/00* (2013.01)

(58) Field of Classification Search
CPC ...... C12M 33/04; C12M 23/40; C12M 29/00; C12M 39/00; B01L 2400/0487; B01L 2400/06; B01L 3/021
See application file for complete search history.

(56) References Cited

U.S. PATENT DOCUMENTS 5,229,074 A * 7/1993 Heath ................ G01N 35/1004
422/67
8,449,840 B2 * 5/2013 Saegusa ............. G01N 35/1009
422/106

(Continued)

FOREIGN PATENT DOCUMENTS

| CN | 101370928 A | 2/2009 |
| JP | 2016-112012 A | 6/2016 |
| WO | 2019/176093 A1 | 9/2019 |

OTHER PUBLICATIONS

Office Action in corresponding Chinese Patent Application No. 201980098325.9 dated Dec. 11, 2023, with English machine translation.

(Continued)

*Primary Examiner* — Liban M Hassan
(74) *Attorney, Agent, or Firm* — Renner, Otto, Boisselle & Sklar, LLP

(57) ABSTRACT

A cell collecting device include a pipette tip that sucks substances in a cell culture container, a first valve connected to the pipette tip through a first flow path, a first pump connected to the first valve through a second flow path, and a second pump connected to the first valve through a third flow path. In a remove mode, the first valve is switched to connect the first flow path and the second flow path to each other and disconnect the third flow path, and the first pump is driven to discharge waste in the cell culture container, that has been sucked from the pipette tip, from a drain of the first pump through the first flow path and the second flow path, and in a picking mode, the first valve is switched to connect the first flow path and the third flow path to each other and disconnect the second flow path, and the second pump is driven to suck cells in the cell culture container using the pipette tip.

4 Claims, 7 Drawing Sheets

(56)　　　　　　References Cited

U.S. PATENT DOCUMENTS

| | | |
|---|---|---|
| 2010/0317102 A1 | 12/2010 | Suzuki et al. |
| 2013/0344597 A1 | 12/2013 | Suzuki et al. |
| 2016/0169775 A1 | 6/2016 | Kei |
| 2020/0377833 A1 | 12/2020 | Inoue |

OTHER PUBLICATIONS

International Search Report for corresponding Application No. PCT/JP2019/029514, mailed Sep. 17, 2019.
Written Opinion for corresponding Application No. PCT/JP2019/029514, mailed Sep. 17, 2019 (English machine translation).

* cited by examiner

F I G. 1
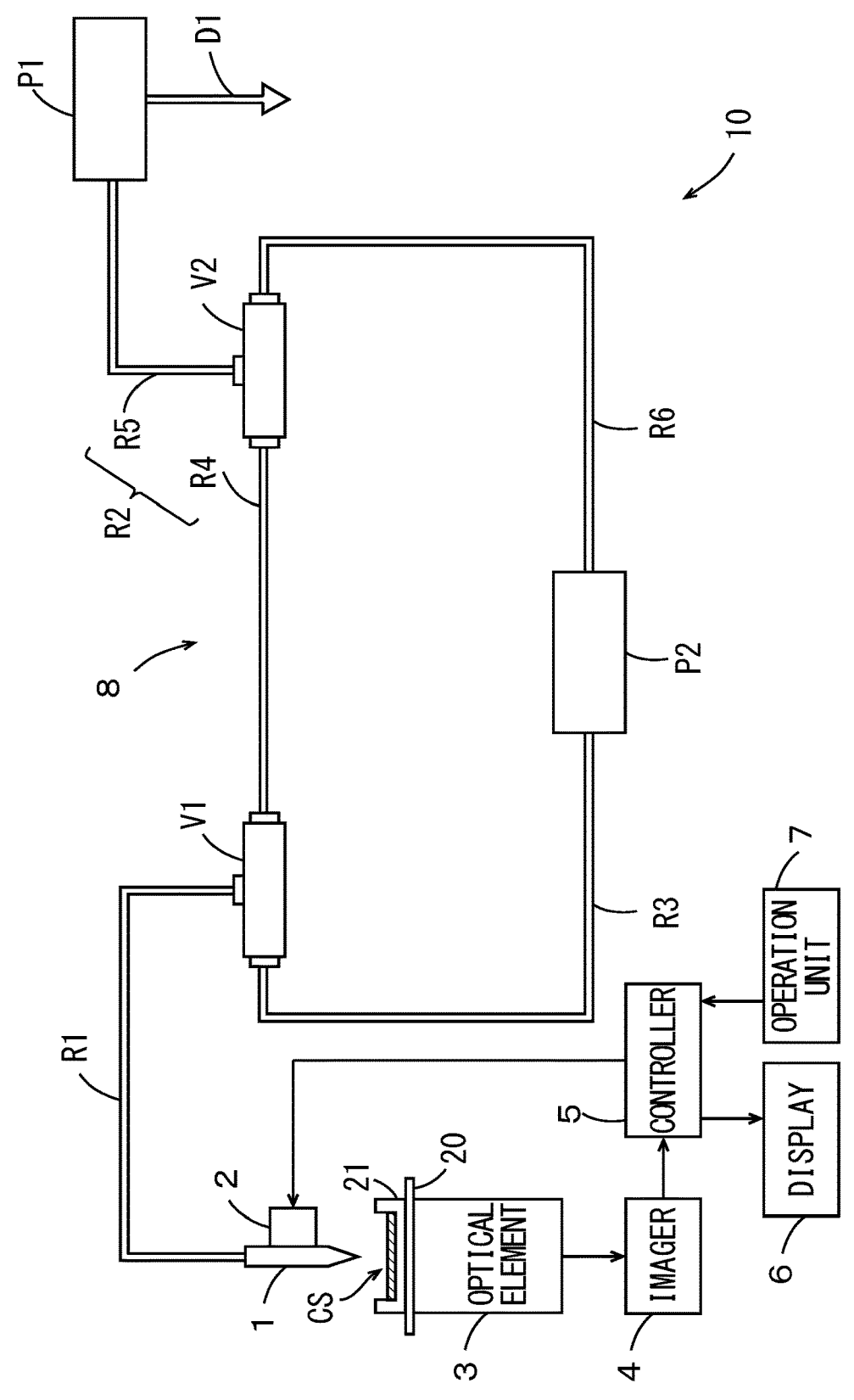

F I G. 2
REMOVE MODE
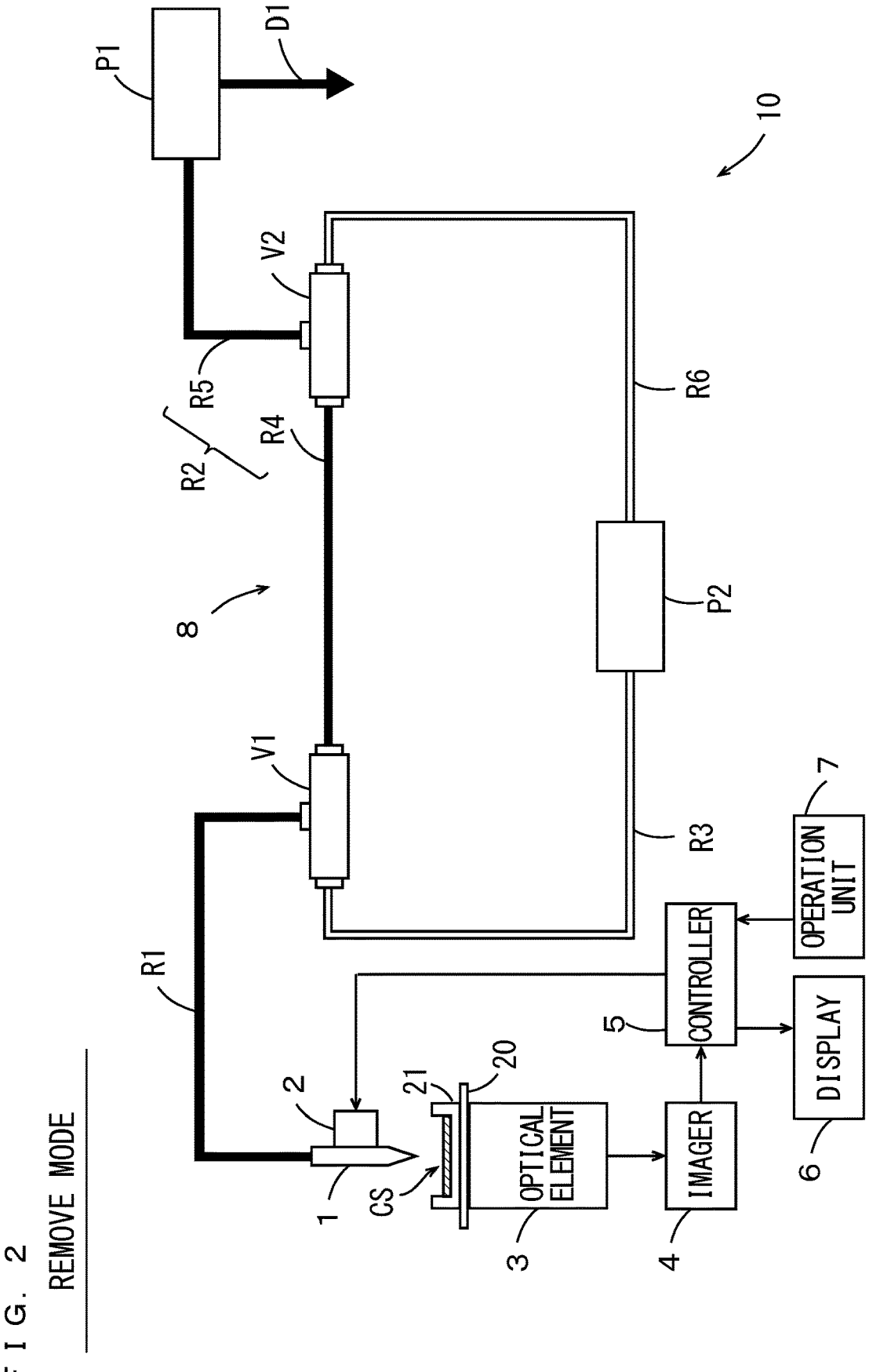

F I G . 3
CLEANING MODE
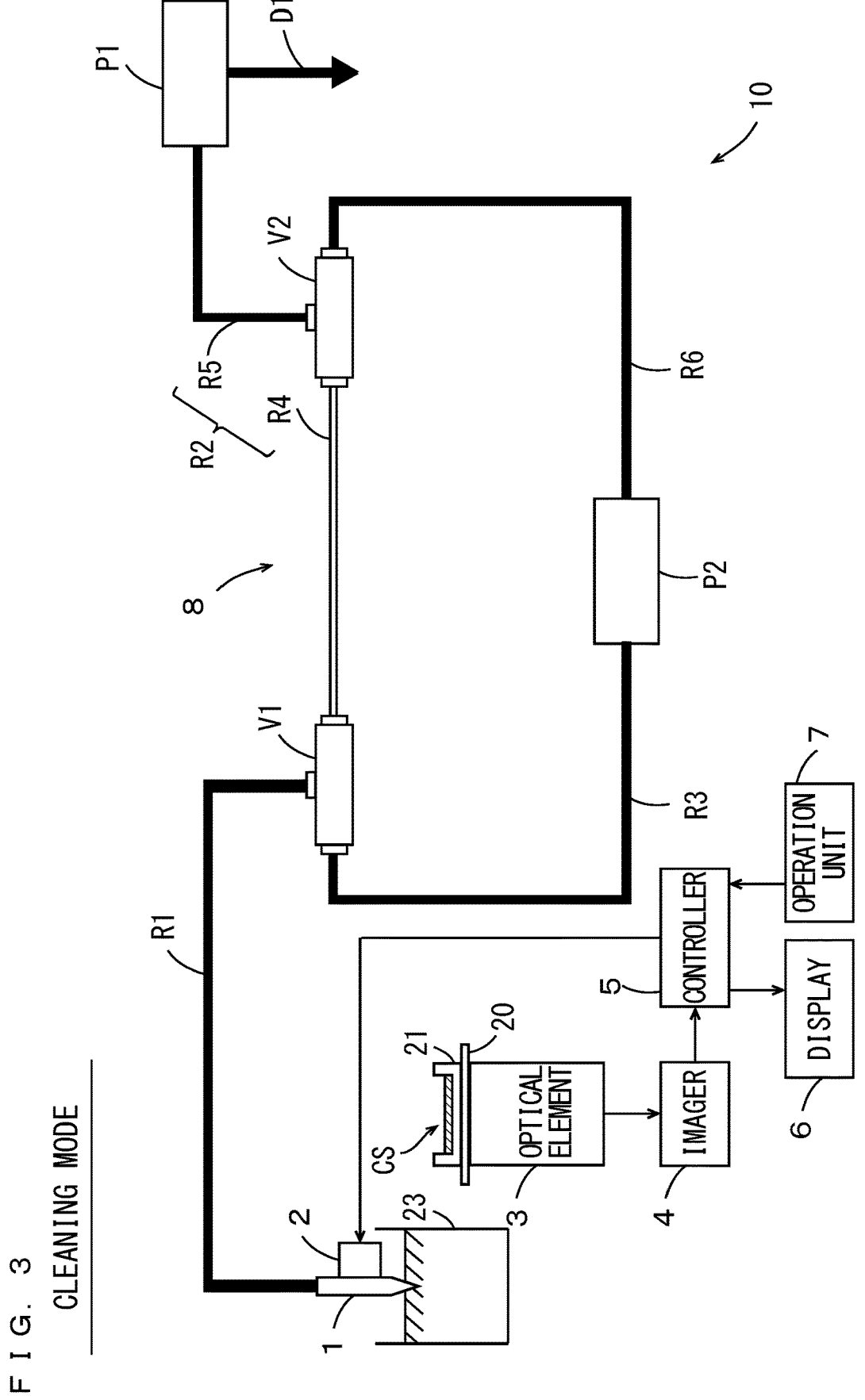

F I G. 4
PICKING MODE
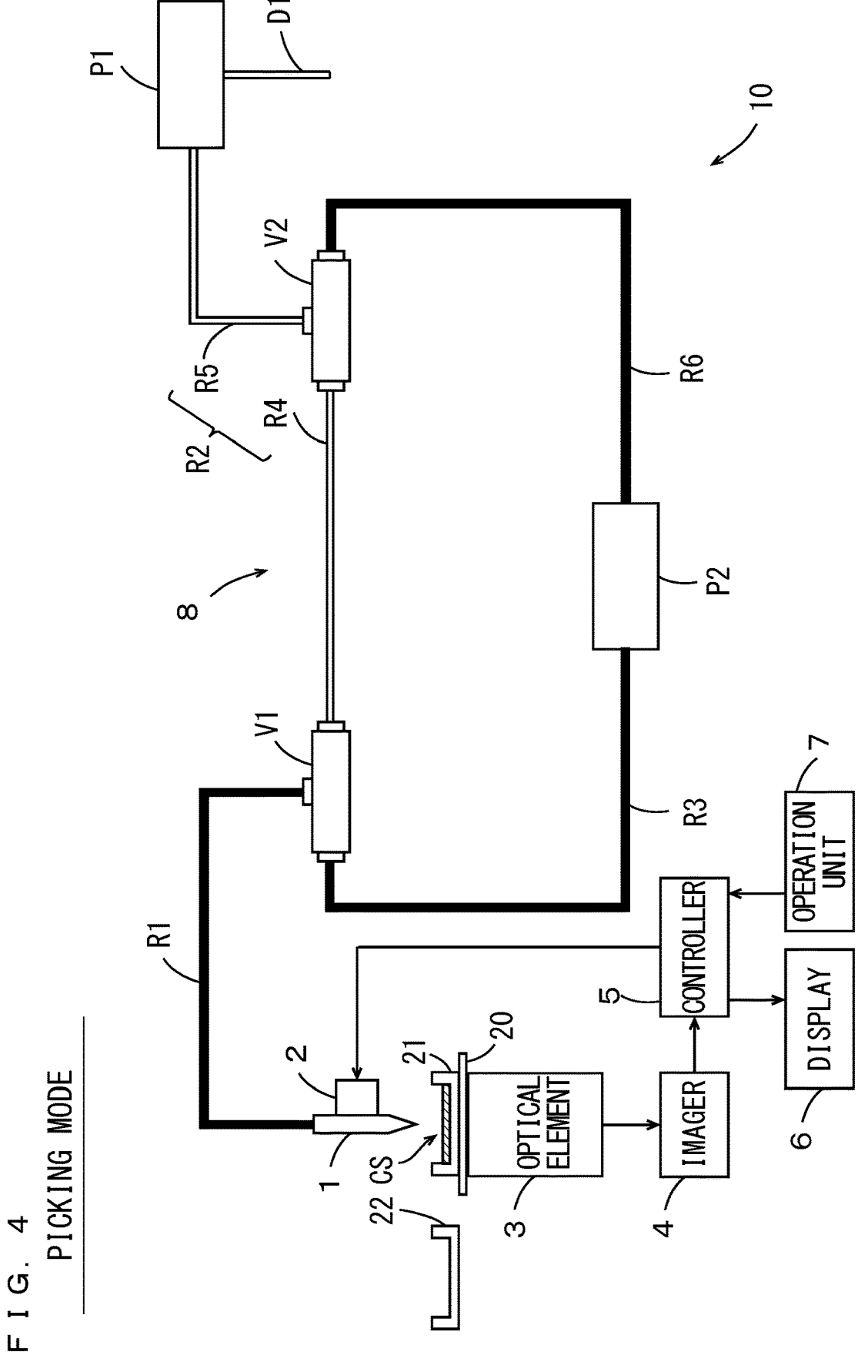

F I G. 5

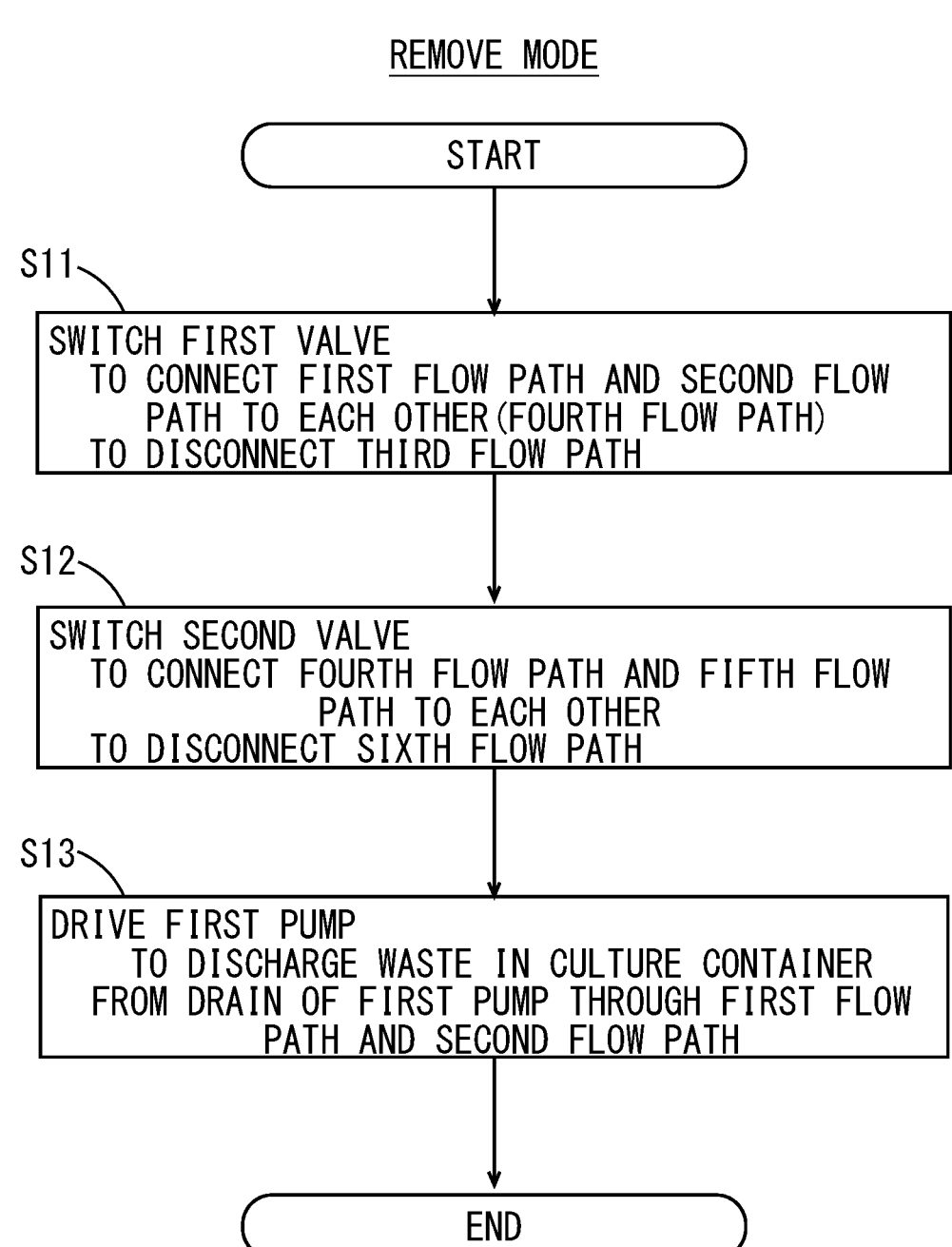

REMOVE MODE

START

S11
SWITCH FIRST VALVE
    TO CONNECT FIRST FLOW PATH AND SECOND FLOW
        PATH TO EACH OTHER(FOURTH FLOW PATH)
    TO DISCONNECT THIRD FLOW PATH

S12
SWITCH SECOND VALVE
    TO CONNECT FOURTH FLOW PATH AND FIFTH FLOW
                PATH TO EACH OTHER
    TO DISCONNECT SIXTH FLOW PATH

S13
DRIVE FIRST PUMP
    TO DISCHARGE WASTE IN CULTURE CONTAINER
    FROM DRAIN OF FIRST PUMP THROUGH FIRST FLOW
            PATH AND SECOND FLOW PATH

END

F I G.  6

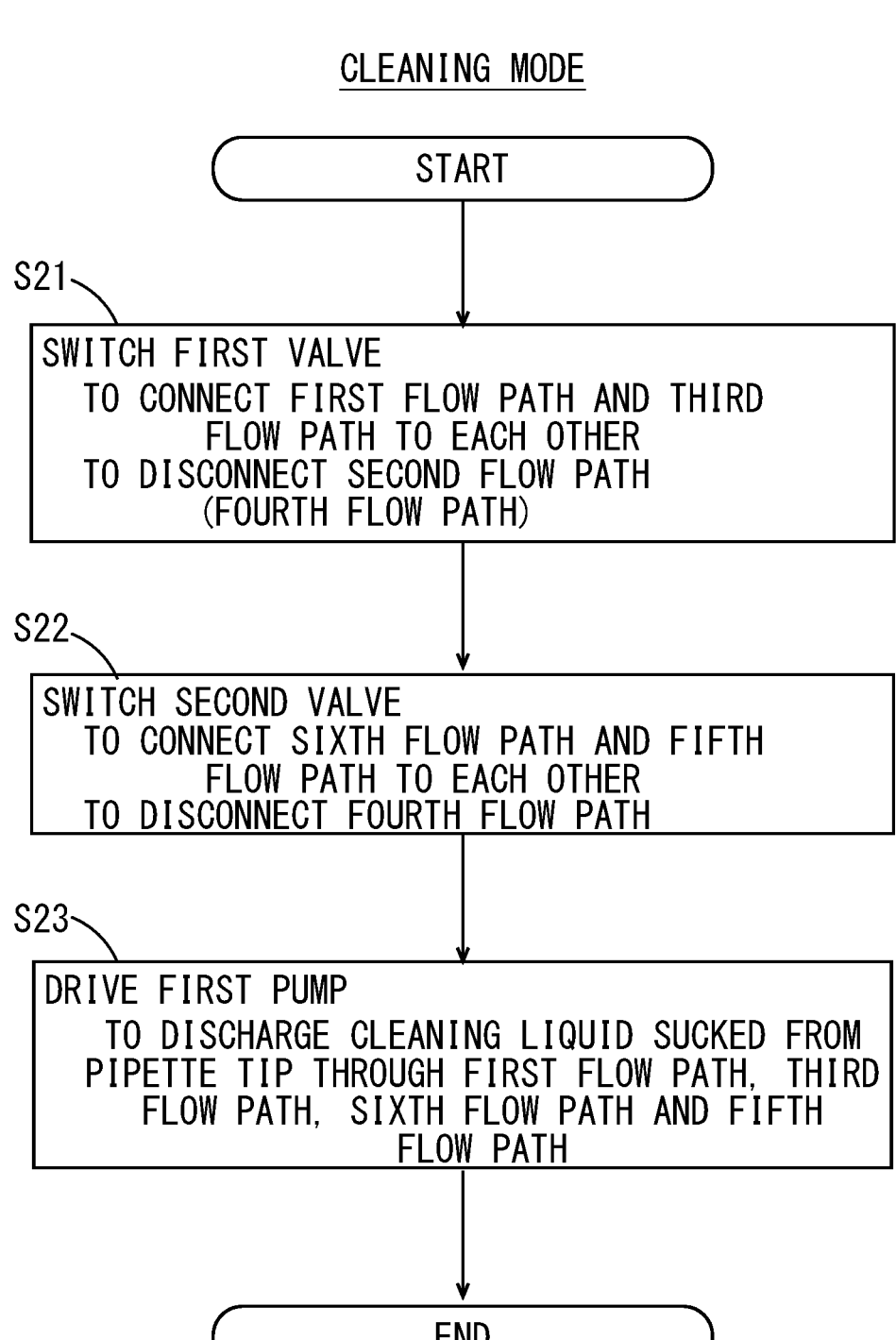

CLEANING MODE

START

S21
SWITCH FIRST VALVE
   TO CONNECT FIRST FLOW PATH AND THIRD
      FLOW PATH TO EACH OTHER
   TO DISCONNECT SECOND FLOW PATH
      (FOURTH FLOW PATH)

S22
SWITCH SECOND VALVE
   TO CONNECT SIXTH FLOW PATH AND FIFTH
      FLOW PATH TO EACH OTHER
   TO DISCONNECT FOURTH FLOW PATH

S23
DRIVE FIRST PUMP
   TO DISCHARGE CLEANING LIQUID SUCKED FROM
   PIPETTE TIP THROUGH FIRST FLOW PATH,  THIRD
      FLOW PATH,  SIXTH FLOW PATH AND FIFTH
         FLOW PATH

END

F I G. 7
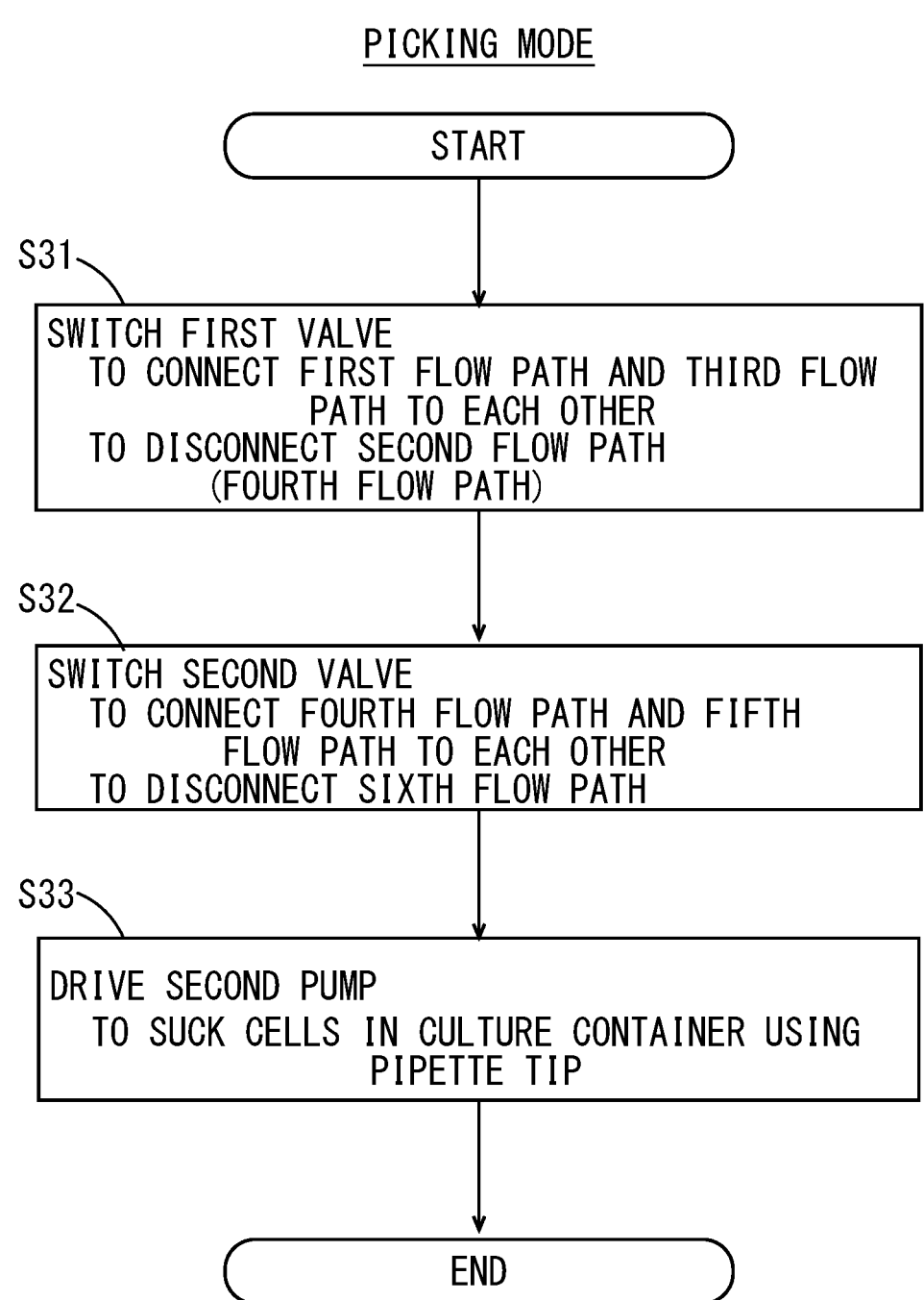
PICKING MODE
START
S31
SWITCH FIRST VALVE
    TO CONNECT FIRST FLOW PATH AND THIRD FLOW
                PATH TO EACH OTHER
    TO DISCONNECT SECOND FLOW PATH
             (FOURTH FLOW PATH)
S32
SWITCH SECOND VALVE
    TO CONNECT FOURTH FLOW PATH AND FIFTH
            FLOW PATH TO EACH OTHER
    TO DISCONNECT SIXTH FLOW PATH
S33
DRIVE SECOND PUMP
    TO SUCK CELLS IN CULTURE CONTAINER USING
                PIPETTE TIP
END

CELL COLLECTING DEVICE AND CELL COLLECTING METHOD

TECHNICAL FIELD

The present invention relates to a cell collecting device and a cell collecting method with which the cell collecting device is used.

BACKGROUND ART

An operator generally manually picks cells as a method of picking specific cells from a cell culture container. The operator sucks specific cells manually by using a sucking tool such as a pipette while checking the position of the specific cells in the cell culture container with a microscope. Such work requires skill, and it is not a method that can be easily performed by anyone.

As such, a cell sucking system for assisting cell picking work has been suggested in Patent Document 1. A system that is suggested in the Patent Document 1 includes a transporter that three-dimensionally moves a sucker having an end to which a pipette tip is attached and a detector that optically detects the end of the pipette tip. This device moves the position of the end of the pipette tip to the position of the specific cells using the transporter while detecting the end of the pipette tip using the detector.

[Patent Document 1] JP 2016-112012 A

SUMMARY OF INVENTION

Technical Problem

The cell sucking system suggested in Patent Document 1 can assist the operator who picks cells. A method of collecting cells in the cell culture container includes a method of removing waste in the cell culture container and leaving specific cells in the cell culture container in addition to the method of picking specific cells as described above. These methods of collecting cells in the cell culture container are still a burdensome work for the operator, and improvement is desirable.

An object of the present invention is to reduce a burden on an operator who collects cells in a cell culture container.

Solution to Problem

A cell collecting device according to one aspect of the present invention includes a pipette tip that sucks substances in a cell culture container, a first valve connected to the pipette tip through a first flow path, a first pump connected to the first valve through a second flow path, and a second pump connected to the first valve through a third flow path. In a remove mode, the first valve is switched to connect the first flow path and the second flow path to each other and disconnect the third flow path, and the first pump is driven to discharge waste in the cell culture container, that has been sucked from the pipette tip, from a drain of the first pump through the first flow path and the second flow path, and in a picking mode, the first valve is switched to connect the first flow path and the third flow path to each other and disconnect the second flow path, and the second pump is driven to suck cells in the cell culture container using the pipette tip.

Advantageous Effects of Invention

The present invention can reduce a burden on an operator who collects cells in a culture container.

BRIEF DESCRIPTION OF THE DRAWINGS

FIG. 1 is an overview of a cell collecting device according to the present embodiment.

FIG. 2 is a diagram showing the cell collecting device running in a remove mode.

FIG. 3 is a diagram showing the cell collecting device running in a cleaning mode.

FIG. 4 is a diagram showing the cell collecting device running in a picking mode.

FIG. 5 is a flowchart showing the behavior in the remove mode.

FIG. 6 is a flowchart showing the behavior in the cleaning mode.

FIG. 7 is a flowchart showing the behavior in the picking mode.

DESCRIPTION OF EMBODIMENTS

The configuration of a cell collecting device according to embodiments of the present invention will now be described below with reference to the attached drawings.

(1) Overall Configuration of Cell Collecting Device

FIG. 1 is an overview of the cell collecting device 10 according to the present embodiment. The cell collecting device 10 of the present embodiment includes three modes: a remove mode, a cleaning mode and a picking mode. The remove mode is a mode for collection of cells by suction and removal of waste in a cell culture container 21 and leaving specific cells in the cell culture container 21. The cleaning mode is a mode for cleaning a flow path included in the cell collecting device 10. The picking mode is a mode for collection of cells by suction of specific cells in the cell culture container 21.

The cell collecting device 10 includes a pipette tip 1, a driver 2, an optical element 3, an imager 4, a controller 5, a display 6, an operation unit 7 and a flow path 8. The pipette tip 1 sucks waste in the cell culture container 21 in the remove mode and sucks specific cells in the cell culture container 21 in the picking mode. The pipette tip 1 sucks a cleaning liquid in the cleaning mode. A first flow path R1 is connected to the pipette tip 1.

The driver 2 moves the pipette tip 1 in a three-dimensional direction. The driver 2 includes a rotation driver for rotation in a horizontal plane, a rotation driver for rotation in a vertical plane and a movement driver for movement in a vertical direction, for example. The controller 5 controls the cell collecting device 10. With the control of the controller 5, the driver 2 moves the pipette tip 1.

The optical element 3 optically detects an end of the pipette tip 1. The optical element 3 includes a microscope the field of view of which is located above a mounting stage 20. An image of the end of the pipette tip 1 detected by the optical element 3 is picked up by the imager 4. The imager 4 is an imaging device such as a CCD (Charge Coupled Device).

An image of the end of the pipette tip 1 picked up by the imager 4 is supplied to the controller 5. The controller 5 acquires the image of the end of the pipette tip 1 and displays the image of the end of the pipette tip 1 in the display 6. The display 6 is a liquid crystal display, for example. An image of the end of the pipette tip 1 and an image of a culture solution CS including cells contained in the cell culture container 21 are included in images displayed in the display 6. An operator can identify the positional relationship between the pipette tip 1 and cells by making reference to the images.

The operation unit 7 includes an operation member for moving the pipette tip 1 in the three-dimensional direction and an operation member for causing the pipette tip 1 to perform sucking work and ejecting work. The operator operates the operation unit 7 to move the end of the pipette tip 1 while making reference to the images of the end of the pipette tip 1 and the culture solution CS including cells that are displayed in the display 6. Further, the operator performs the sucking work or the ejecting work with respect to the pipette tip 1 while making reference to the images of the end of the pipette tip 1 and the culture solution CS including cells that are displayed in the display 6.

The flow path 8 includes a first valve V1, a second valve V2, a first pump P1 and a second pump P2. The pipette tip 1 and the first valve V1 are connected to each other via the first flow path R1. The first valve V1 and the second valve V2 are connected to each other via a fourth flow path R4. The second valve V2 and the first pump P1 are connected to each other via a fifth flow path R5. The first valve V1 and the second pump P2 are connected to each other via a third flow path R3. The second pump P2 and the second valve V2 are connected to each other via a sixth flow path R6. The fourth flow path R4 and the fifth flow path R5 constitutes a second flow path R2.

The first flow path R1 is connected to a suction port of the pipette tip 1, and the culture solution CS including waste sucked by the pipette tip 1 flows into the first flow path R1 in the remove mode. Further, in the remove mode, the culture solution CS including waste flows into the first flow path R1 and the second flow path R2 (the fourth flow path R4 and the fifth flow path R5). Further, in the cleaning mode, the cleaning liquid sucked by the pipette tip 1 flows into the first flow path R1. Further, in the cleaning mode, the cleaning liquid flows into the first flow path R1, the third flow path R3, the sixth flow path R6 and the fifth flow path R5. Further, in the picking mode, the first flow path R1, the third flow path R3 and the sixth flow path R6 are filled with the culture solution in advance.

The first valve V1 is a valve including three ports to which the first flow path R1, the fourth flow path R4 (the second flow path R2) and the third flow path R3 are respectively connected. The first valve V1 can be switched between a first switch state in which the first valve V1 connects the first flow path R1 and the fourth flow path R4 (the second flow path R2) to each other and disconnects the third flow path R3, and a second switch state in which the first valve V1 connects the first flow path R1 and the third flow path R3 to each other and disconnects the fourth flow path R4 (the second flow path R2). With the control of the controller 5, the first valve V1 is switched between the first switch state and the second switch state.

The second valve V2 is a valve including three ports to which the fourth flow path R4, the fifth flow path R5 and the sixth flow path R6 are respectively connected. The second valve V2 can be switched between the first switch state in which the second valve V2 connects the fourth flow path R4 and the fifth flow path R5 to each other and disconnects the sixth flow path R6 and the second switch state in which the second valve V2 connects the sixth flow path R6 and the fifth flow path R5 to each other and disconnects the fourth flow path R4. With the control of the controller 5, the second valve V2 is switched between the first switch state and the second switch state.

The first pump P1 is a motor driven in the remove mode and in the cleaning mode. The first pump P1 is driven by control of the controller 5. The first pump P1 is a motor that has large capacity and is powerful as compared to the second pump P2. In the present embodiment, a diaphragm pump is used as the first pump P1. In the remove mode, the first pump P1 sucks the culture solution CS including waste through the first flow path R1 and the second flow path R2 (the fourth flow path R4 and the fifth flow path R5). In the cleaning mode, the first pump P1 sucks the cleaning liquid through the first flow path R1, the third flow path R3, the sixth flow path R6 and the fifth flow path R5. The first pump P1 discharges the sucked culture solution CS including waste, the cleaning liquid or the like from a drain D1.

The second pump P2 is a motor driven in the picking mode. The second pump P2 is driven by control of the controller 5. The second pump P2 has is a motor that has small capacity and controls a suction amount and an ejection amount with high accuracy as compared to the first pump P1. In the present embodiment, a plunger pump is used as the second pump P2. In the picking mode, since sucking work is performed in units of one cell, for example, an amount of culture solution sucked by the second pump P2 is extremely small. The second pump P2 sucks the culture solution from the third flow path R3 during the sucking work in the picking mode. The second pump P2 discharges the culture solution sucked into a cylinder to the third flow path R3 during the ejecting work in the picking mode.

(2) Remove Mode

Next, the behavior of the cell collecting device 10 of the present embodiment in the remove mode will be described with reference to FIGS. 2 and 5. FIG. 2 is a diagram showing the cell collecting device 10 that is running in the remove mode. FIG. 5 is a flowchart showing the behavior in the remove mode.

As described above, the remove mode is a mode for collection of cells by suction and removal of waste in the cell culture container 21 and leaving specific cells in the cell culture container 21. As shown in FIG. 2, the cell culture container 21 is placed on an upper portion of the mounting stage 20. The culture solution CS including cells to be collected is contained in the cell culture container 21.

In the step S11 shown in FIG. 5, the controller 5 switches the first valve V1 to connect the first flow path R1 and the second flow path R2 (the fourth flow path R4) to each other and disconnect the third flow path R3. Further, in the step S12, the controller 5 switches the second valve V2 to connect the fourth flow path R4 and the fifth flow path R5 to each other and disconnect the sixth flow path R6. Next, in the step S13, the controller 5 drives the first pump P1 to cause the pipette tip 1 to suck the culture solution CS including waste in the cell culture container 21. The culture solution CS, including waste, sucked by the pipette tip 1 is discharged from the drain D1 of the first pump P1 through the first flow path R1 and the second flow path R2 (the fourth flow path R4 and the fifth flow path R5).

In FIG. 2, the flow path shown in black is a flow path through which the culture solution CS, including waste, sucked by the pipette tip 1 flows. The sucked culture solution CS including waste is discharged from the drain D1 by a driving force of the first pump P1. With repetition of this operation, cells to be collected remain in the cell culture container 21.

(3) Cleaning Mode

Next, the behavior of the cell collecting device 10 of the present embodiment in the cleaning mode will be described below with reference to FIGS. 3 and 6. FIG. 3 is a diagram showing the cell collecting device 10 running in the cleaning mode. FIG. 6 is a flowchart showing the behavior in the cleaning mode.

The cleaning mode is a mode for mainly cleaning the flow path including the first flow path R1. The first flow path R1 is a flow path commonly used in the remove mode and the picking mode. For example, after the cell collecting work is performed in the remove mode, the cell collecting device 10 runs in the cleaning mode before the cell collecting work is performed in the picking mode. As shown in FIG. 3, in the cleaning mode, the pipette tip 1 is moved to be arranged in a cleaning liquid tank 23. The pipette tip 1 sucks the cleaning liquid by performing the sucking work. The cleaning liquid sucked by the pipette tip 1 flows into the first flow path R1.

In the step S21 shown in FIG. 6, the controller 5 switches the first valve V1 to connects the first flow path R1 to the third flow path R3 and disconnect the second flow path R2 (the fourth flow path R4). Further, in the step S22, the controller 5 switches the second valve V2 to connect the sixth flow path R6 and the fifth flow path R5 to each other and disconnect the fourth flow path R4. Next, in the step S23, the controller 5 drives the first pump P1 to discharge the cleaning liquid, that has been sucked from the pipette tip 1, from the drain D1 of the first pump P1 through the first flow path R1, the third flow path R3, the sixth flow path R6 and the fifth flow path R5.

In the FIG. 3, the flow path shown in black is a flow path through which the cleaning liquid sucked by the pipette tip 1 flows. The sucked cleaning liquid is discharged from the drain D1 by a driving force of the first pump P1. With this operation, waste remaining in the first flow path R1 in the remove mode is removed, for example. Thus, when cells are collected in the picking mode afterward, contamination caused by waste remaining in the remove mode can be prevented.

In the cleaning mode, maximum movement of a plunger of the second pump P2 in an ejection direction is preferable. Thus, the cleaning liquid flowing through the first flow path R1 and the third flow path R3 because of a sucking force of the first pump P1 flows into the sixth flow path R6 without entering the cylinder of the second pump P2. Thus, flowing waste that is mixed with the cleaning liquid is prevented from entering the cylinder of the second pump P2.

(4) Picking Mode

Next, the behavior of the cell collecting device 10 of the present embodiment in the picking mode will be described with reference to FIGS. 4 and 7. FIG. 4 is a diagram showing the cell collecting device 10 running in the picking mode. FIG. 7 is a flowchart showing the behavior in the picking mode.

As described above, the picking mode is a mode for collection of cells by suction of specific cells in the cell culture container 21. As shown in FIG. 4, the cell culture container 21 is placed on the upper portion of the mounting stage 20. The culture solution CS including cells to be collected is contained in the cell culture container 21.

The first flow path R1, the third flow path R3 and the sixth flow path R6 are first filled with the culture solution before the cell collecting work is performed in the picking mode, whereby the cell collecting device prepares for the picking mode. Specifically, the pipette tip 1 is arranged in a separately prepared container containing the culture solution. The first valve V1 and the second valve V2 are switched, and the fourth flow path R4 is disconnected similarly to the cleaning mode, and then the first pump P1 is driven. Thus, the culture solution sucked by the pipette tip 1 flows into the first flow path R1, the third flow path R3, the sixth flow path R6 and the fifth flow path R5. Thus, the first flow path R1, the third flow path R3 and the sixth flow path R6 are filled with the culture solution.

In the step S31 shown in FIG. 7, the controller 5 switches the first valve V1 to connect the first flow path R1 and the third flow path R3 to each other and disconnect the second flow path R2 (the fourth flow path R4). Further, in the step S32, the controller 5 switches the second valve V2 to connect the fourth flow path R4 and the fifth flow path R5 to each other and disconnect the sixth flow path R6. Next, in the step S33, the controller 5 drives the second pump P2 to cause the second pump P2 to perform the sucking work. Thus, cells in the cell culture container 21 are sucked by the pipette tip 1. Cells that have been sucked by the pipette tip 1 and are to be collected are held in the end of the pipette tip 1. Further, a small amount of the culture solution in the third flow path R3 is held in the cylinder of the second pump P2 by the sucking work of by the pipette tip 1. When the second pump P2 performs the sucking work, a sucking force is applied to both of the third flow path R3 and the sixth flow path R6. However, because the second valve V2 is switched to disconnect the sixth flow path R6, the culture solution in the third flow path R3 is sucked into the second pump P2 by the sucking work of the second pump P2.

Thereafter, the pipette tip 1 is moved to the position of a collection container 22 shown in FIG. 4. Then, the controller 5 controls the second pump P2 to cause the second pump P2 to perform the ejecting work. Thus, cells held in the end of the pipette tip 1 are transferred to the collection container 22. When the second pump P2 performs the ejecting work, the pressure is applied to both of the third flow path R3 and the sixth flow path R6. However, because the second valve V2 is switched to disconnect the sixth flow path R6, a large amount of the culture solution ejected from the second pump P2 is pushed out to the third flow path R3 by the ejecting work of the second pump P2. Thus, the pressure is applied to the first flow path R1 through the third flow path R3 by the ejecting work of the second pump P2, and cells held in the end of the pipette tip 1 are ejected.

In FIG. 4, the flow path shown in black is the flow path filled with the culture solution in the picking mode. The cells that have been sucked by the sucking work of the second pump P2 are held in the end of the pipette tip 1. Cells held in the pipette tip 1 are transferred to the collection container 22 by the ejecting work of the second pump P2.

As described above, the cell collecting device of the present embodiment can run in the remove mode and the picking mode by switching of the first valve V1 and the second valve V2. This reduces a work load on the operator who performs the cell collecting work. Further, the cell collecting device of the present embodiment can run in the cleaning mode by switching of the first valve V1 and the second valve V2. Thus, when cells are collected in the picking mode, for example, contamination caused by remaining waste in the remove mode can be prevented.

(5) Other Embodiments

In the above-mentioned embodiment, the diaphragm pump is used as the first pump P1, and the plunger pump is used as the second pump P2. Pumps that are used as the first pump P1 and the second pump P2 are not limited in particular, and other pumps may be used. However, since the first pump P1 is used for removal of waste in the remove mode and suction of the cleaning liquid in the cleaning mode, a pump that has relatively large capacity and is powerful is preferably used as the first pump P1. Since the second pump P2 needs to perform the sucking work in units of one cell or in units of tissues in a cell in the picking mode, a pump that can control a suction amount and an ejection amount with high accuracy is preferably used as the second pump P2.

While having three modes which are the remove mode, the cleaning mode and the picking mode by way of example in the above-mentioned embodiment, the cell collecting device 10 may be configured not to have the cleaning mode but have the remove mode and the picking mode. In this case, when the remove mode is switched to the picking mode, the flow path 8 may be cleaned by another method. In a case where the cell collecting device 10 does not have the cleaning mode, the second valve V2 and the sixth flow path R6 can be unprovided. In this case, the first valve V1 and the first pump P1 may be directly connected to each other.

As each of constituent elements recited in the claims, various other elements having configurations or functions described in the claims can be also used.

While preferred embodiments of the present invention have been described above, it is to be understood that variations and modifications will be apparent to those skilled in the art without departing the scope and spirit of the present invention. The scope of the present invention, therefore, is to be determined solely by the following claims.

(6) Aspects

It is understood by those skilled in the art that the plurality of above-mentioned illustrative embodiments are specific examples of the below-mentioned aspects.

(Item 1) A cell collecting device according to one aspect includes a pipette tip that sucks substances in a cell culture container, a first valve connected to the pipette tip through a first flow path, a first pump connected to the first valve through a second flow path, and a second pump connected to the first valve through a third flow path, wherein in a remove mode, the first valve is switched to connect the first flow path and the second flow path to each other and disconnect the third flow path, and the first pump is driven to discharge waste in the cell culture container, that has been sucked from the pipette tip, from a drain of the first pump through the first flow path and the second flow path, and in a picking mode, the first valve is switched to connect the first flow path and the third flow path to each other and disconnect the second flow path, and the second pump is driven to suck cells in the cell culture container using the pipette tip.

With this cell collecting device, cells can be collected in any one of the remove mode and the picking mode by switching of the first valve. This reduces a burden on an operator who collects cells in the cell culture container.

(Item 2) The cell collecting device according to item 1, wherein the second flow path may include a fourth flow path and a fifth flow path, and the cell collecting device may further include a second valve connected to the first valve through the fourth flow path, connected to the first pump through the fifth flow path and connected to the second pump through the sixth flow path, in a cleaning mode, the first valve may be switched to connect the first flow path and the third flow path to each other and disconnect the fourth flow path, the second valve may be switched to connect the sixth flow path and the fifth flow path to each other and disconnect the fourth flow path, and the first pump may be driven to discharge a cleaning liquid, that has been sucked from the pipette tip, from a drain of the first pump through the first flow path, the third flow path, the sixth flow path and the fifth flow path.

With this cell collecting device, the flow path used for collection of cells can be cleaned by switching of the first valve and the second valve. Thus, the flow paths including the first flow path commonly used in the remove mode and the picking mode in the cell collecting device can be cleaned.

(Item 3) The cell collecting device according to item 2, wherein the first flow path, the third flow path and the sixth flow path may be filled with a culture liquid in advance at start of the picking mode.

Because the flow path is filled with the culture solution at the start of the picking mode, the suction amount of the second pump can be adjusted accurately.

(Item 4) A cell collecting method according to one aspect that is performed in a cell collecting device, wherein the cell collecting device may include a pipette tip that sucks substances in a cell culture container, a first valve connected to the pipette tip through a first flow path, a first pump connected to the first valve through a second flow path, and a second pump connected to the first valve through a third flow path, and the cell collecting method may include, in a remove mode, switching the first valve to connect the first flow path and the second flow path to each other and disconnect the third flow path, and driving the first pump to discharge waste in the cell culture container, that has been sucked from the pipette tip, from a drain of the first pump through the first flow path and the second flow path, and in a picking mode, switching the first valve to connect the first flow path and the third flow path to each other and disconnect the second flow path, and driving the second pump to suck cells in the cell culture container using the pipette tip.

(Item 5) The cell collecting method according to item 4, wherein the second flow path may include a fourth flow path and a fifth flow path, and the cell collecting device may further include a second valve connected to the first valve through the fourth flow path, connected to the first pump through the fifth flow path and connected to the second pump through the sixth flow path, and the cell picking method may include, in a cleaning mode, switching the first valve to connect the first flow path and the third flow path to each other and disconnect the fourth flow path, switching the second valve to connect the sixth flow path and the fifth flow path to each other and disconnect the fourth flow path, and driving the first pump to discharge a cleaning liquid, that has been sucked from the pipette tip, from a drain of the first pump through the first flow path, the third flow path, the sixth flow path and the fifth flow path.

The invention claimed is:
1. A cell collecting device comprising:
a controller;
a pipette tip that moves under the control of the controller and sucks substances in a cell culture container;

a first valve connected to the pipette tip through a first flow path;

a first pump connected to the first valve through a second flow path; and a second pump connected to the first valve through a third flow path, wherein in a remove mode, which is a collection mode that recovers the cells in the cell culture container by Sucking and removing impurities in the cell culture container and leaving specific cells in the cell culture container, the first valve is switched under the control of the controller to connect the first flow path and the second flow path to each other and disconnect the third flow path, and the first pump is driven to discharge waste in the cell culture container, that has been sucked from the pipette tip, from a drain of the first pump through the first flow path and the second flow path, and in a picking mode, which is a collection mode that recovers the cells to a collection container by sucking specific cells in the cell culture container by the pipette up, the first valve is switched under the control of the controller to connect the first flow path and the third flow path to each other and disconnect the second flow path, and the second pump is driven to suck cells in the cell culture container using the pipette tip and the controller causes the second pump to perform a discharge operation, and the cells held in the pipette tip are delivered to the collection container from a tip end of the pipette tip by the discharge operation of the second pump, and wherein the controller is configured to control the pipette tip, first valve, first pump, and second pump.

2. The cell collecting device according to claim 1, wherein
the second flow path includes a fourth flow path and a fifth flow path, and
the cell collecting device further includes a second valve connected to the first valve through the fourth flow path, connected to the first pump through the fifth flow path and connected to the second pump through the sixth flow path,
in a cleaning mode, the first valve is switched under the control of the controller to connect the first flow path and the third flow path to each other and disconnect the fourth flow path, the second valve is switched under the control of the controller to connect the sixth flow path and the fifth flow path to each other and disconnect the fourth flow path, and the first pump is driven under the control of the controller to discharge a cleaning liquid, that has been sucked from the pipette tip, from a drain of the first pump through the first flow path, the third flow path, the sixth flow path and the fifth flow path.

3. The cell collecting device according to claim 2, wherein
the first flow path, the third flow path and the sixth flow path are filled with a culture liquid in advance at start of the picking mode.

4. A cell collecting device comprising:
a pipette tip that sucks substances in a cell culture container;
a first valve connected to the pipette tip through a first flow path;
a first pump connected to the first valve through a second flow path; and
a second pump connected to the first valve through a third flow path, wherein
in a remove mode, the first valve is switched to connect the first flow path and the second flow path to each other and disconnect the third flow path, and the first pump is driven to discharge waste in the cell culture container, that has been sucked from the pipette tip, from a drain of the first pump through the first flow path and the second flow path, and
in a picking mode, the first valve is switched to connect the first flow path and the third flow path to each other and disconnect the second flow path, and the second pump is driven to suck cells in the cell culture container using the pipette tip, wherein
the second flow path includes a fourth flow path and a fifth flow path, and
the cell collecting device further includes a second valve connected to the first valve through the fourth flow path, connected to the first pump through the fifth flow path and connected to the second pump through the sixth flow path,
in a cleaning mode, the first valve is switched to connect the first flow path and the third flow path to each other and disconnect the fourth flow path, the second valve is switched to connect the sixth flow path and the fifth flow path to each other and disconnect the fourth flow path, and the first pump is driven to discharge a cleaning liquid, that has been sucked from the pipette tip, from a drain of the first pump through the first flow path, the third flow path, the sixth flow path and the fifth flow path.

*    *    *    *    *